United States Patent
Thomé et al.

(10) Patent No.: US 10,159,545 B2
(45) Date of Patent: Dec. 25, 2018

(54) SCANBODY

(71) Applicant: JJGC INDÚSTRIA E COMÉRCIO DE MATERIAIS DENTÁRIOS S.A., Curitiba (BR)

(72) Inventors: Geninho Thomé, Curitiba (BR); Thiago Vieira Thomé, Curitiba (BR); Felix Andreas Mertin, Curitiba (BR)

(73) Assignee: JJGC INDÚSTRIA E COMÉRCIO DE MATERIAIS DENTÁRIOS S.A., Curitiba (BR)

( * ) Notice: Subject to any disclaimer, the term of this patent is extended or adjusted under 35 U.S.C. 154(b) by 0 days.

(21) Appl. No.: 15/215,441

(22) Filed: Jul. 20, 2016

(65) Prior Publication Data
US 2017/0027667 A1 Feb. 2, 2017

(30) Foreign Application Priority Data
Jul. 31, 2015 (BR) .......................... 1020150184603

(51) Int. Cl.
*A61C 8/00* (2006.01)
*A61C 9/00* (2006.01)

(52) U.S. Cl.
CPC ............ *A61C 8/0001* (2013.01); *A61C 8/006* (2013.01); *A61C 8/0016* (2013.01); *A61C 8/0068* (2013.01); *A61C 8/0071* (2013.01); *A61C 9/0053* (2013.01)

(58) Field of Classification Search
CPC ..... A61C 8/0001; A61C 8/0016; A61C 8/006; A61C 8/0068; A61C 8/0071; A61C 9/0053; A61C 13/0004

USPC .............................. 433/172–176, 201.1, 213
See application file for complete search history.

(56) References Cited

U.S. PATENT DOCUMENTS

| | | | |
|---|---|---|---|
| 4,575,805 A | 3/1986 | Moermann et al. | |
| 4,742,464 A | 5/1988 | Duret et al. | |
| 4,758,161 A * | 7/1988 | Niznick | A61C 8/0001 433/173 |
| 4,837,732 A | 6/1989 | Brandestini et al. | |
| 4,988,297 A | 1/1991 | Lazzara et al. | |

(Continued)

FOREIGN PATENT DOCUMENTS

| | | |
|---|---|---|
| EP | 2130514 | 12/2009 |
| EP | 2218423 | 8/2010 |

(Continued)

OTHER PUBLICATIONS

European Search Report received from EP Application Serial No. 16181809.1, dated Dec. 2, 35 pages.

*Primary Examiner* — Matthew Nelson
(74) *Attorney, Agent, or Firm* — Arc IP Law, PC; Joseph J. Mayo

(57) ABSTRACT

Embodiments include a scanbody that includes a base that fits in an anti-rotation geometry of a dental implant, and a body that is set to be scanner. The body includes a lateral surface with geometrical elements that allow the identification of information regarding a position, direction and rotation of the scanbody. The body lateral surface does not include any flat portion and includes a first opposing trunconical element, base-to-base, a secondary trunconic element and concave surfaces disposed at the side, including a hole (5) that receives a fixing screw.

9 Claims, 8 Drawing Sheets

(56) References Cited

U.S. PATENT DOCUMENTS

| | | | |
|---|---|---|---|
| 5,145,372 A * | 9/1992 | Daftary | A61C 8/005 |
| | | | 433/173 |
| 5,344,457 A * | 9/1994 | Pilliar | A61C 8/0012 |
| | | | 433/174 |
| 5,547,377 A * | 8/1996 | Daftary | A61C 8/0048 |
| | | | 433/172 |
| 5,829,981 A | 11/1998 | Ziegler | |
| 6,280,195 B1 * | 8/2001 | Broberg | A61C 8/00 |
| | | | 433/201.1 |
| 6,648,643 B2 | 11/2003 | Hollander et al. | |
| 6,991,853 B2 | 1/2006 | Branco de Luca et al. | |
| 8,277,218 B2 * | 10/2012 | D'Alise | A61C 8/0025 |
| | | | 433/174 |
| 8,333,591 B2 * | 12/2012 | Zhao | A61C 8/001 |
| | | | 433/174 |
| 8,480,395 B2 * | 7/2013 | D'Alise | A61C 8/0025 |
| | | | 433/174 |
| 8,480,396 B2 | 7/2013 | Saliger et al. | |
| 8,485,819 B2 * | 7/2013 | Callan | A61C 8/0048 |
| | | | 433/173 |
| 8,747,112 B2 * | 6/2014 | Brun | A61C 8/0001 |
| | | | 433/173 |
| 8,801,435 B2 * | 8/2014 | Jahn | A61C 9/0053 |
| | | | 433/173 |
| 8,920,170 B2 * | 12/2014 | Krivoruk | A61C 8/0048 |
| | | | 433/172 |
| D729,934 S | 5/2015 | Futterknecht et al. | |
| 2002/0106610 A1 * | 8/2002 | Hurson | A61C 8/0001 |
| | | | 433/173 |
| 2004/0209226 A1 * | 10/2004 | Rogers | A61C 8/0001 |
| | | | 433/173 |
| 2007/0298379 A1 * | 12/2007 | D'Alise | A61C 8/0025 |
| | | | 433/174 |
| 2011/0136079 A1 * | 6/2011 | Okazaki | A61C 8/0081 |
| | | | 433/174 |
| 2011/0306014 A1 * | 12/2011 | Conte | A61C 8/0001 |
| | | | 433/173 |
| 2012/0009545 A1 | 1/2012 | Eriksson et al. | |
| 2012/0028214 A1 | 2/2012 | Futterknecht et al. | |
| 2012/0035889 A1 * | 2/2012 | Lawitschka | A61C 8/0001 |
| | | | 703/1 |
| 2013/0209960 A1 * | 8/2013 | Benhamou | A61C 3/02 |
| | | | 433/174 |
| 2014/0124374 A1 * | 5/2014 | Eriksson | A61C 8/0001 |
| | | | 205/112 |
| 2015/0037758 A1 * | 2/2015 | Tatum, Jr. | A61C 8/0022 |
| | | | 433/174 |
| 2016/0213451 A1 * | 7/2016 | Burger | A61C 3/02 |

FOREIGN PATENT DOCUMENTS

| | | |
|---|---|---|
| EP | 2400917 | 1/2012 |
| EP | 2457536 A2 | 5/2012 |
| KR | 101452849 B1 | 10/2014 |

* cited by examiner

SCANBODY

This application claims foreign priority to Brazilian Patent Application Serial No. 1020150184603, filed on 31 Jul. 2015, the specification of which is hereby incorporated herein by reference.

BACKGROUND OF THE INVENTION

Field of the Invention

Embodiments of the invention generally relate to the field of dentistry and, specifically, to printing aided techniques used with dentures and molds for printing. Embodiments include a component that transfers position, direction and rotation information of an implant installed in a patient's mouth or in a mold to be used in scanning equipment.

Description of the Related Art

Generally, dental implants are used as supports to replace one or more missing teeth. The implant, also known as abutment, is typically the first of at least two parts of dental restoration that also includes one or more prosthetic elements fixed to the implant by means of a screw. The prosthetic elements are responsible for aesthetic replacement of missing teeth and usually consist of an intermediate structural component known as a connection; and aesthetic replacement, known as a crown, commonly attached through adhesive or cement suitable for dental use. In some cases only a prosthetic component is used, combining structural and aesthetic function, for one or more missing teeth.

Generally, the success of restoration depends on the stability of the entire set, particularly the absence of relative movement between the abutment and the prosthetic elements. For this purpose, the abutment typically includes, in its upper portion, a hexagonal or octagonal-shaped coupling as an anti-rotation element, or other geometric form to prevent rotation, even amorphous, which is applied directly to a surface or inside of a conical recess usually known as a Morse taper.

Generally, the prosthetic element, in turn, is coupled to the abutment, topically connected, and includes complementary coupling geometry, whether anti-rotation or not (as the case may be), so that when the connection and abutment are coupled in the mouth, the cooperation between the anti-rotation elements prevents the relative movement between these components or, in case of prosthesis supported on multiple implants, the disposition itself of more than one supporting point to prevent the relative movement. Thus, typically, the screw that holds the connection to the abutment is used only to prevent the separation of these two parts and does not prevent the relative rotation movement among them, by minimizing the strain on the screw and expanding its cycle life.

Generally, the presence of these anti-rotation elements requires additional care on the manufacture of prosthetic component so that, when installed, the internal surfaces and external prosthesis remain aligned to those of nearby teeth. For this purpose, as will be discussed herein, it is necessary to measure not only the position (x, y, and z), but also the direction (in angles around each one of the axes x, y, and z), as well as the anti-rotation fixing element alignment in the mouth, that is, in which direction the corners of this anti-rotation element are located such that these measurements are considered in the manufacture of the connection and are reflected on how the aesthetic portion is concocted in relation to underlying anti-rotation element. This occurs because, even if the installation is carefully made to achieve a specific alignment, certain micro movements during the healing phase may lead to loss of alignment.

Generally, when the prosthetic element is supported on multiple implants, for instance, in the case of a prosthetic bridge, the position and direction of the abutment is vital information to avoid prosthesis settlement issues that may occur when, due to misalignment of given connection elements makes up the bridge, the dentist is bound to force or fit the component so that it may be implanted.

Currently, after a period of healing in which the implant remains closed under the gums, it is exposed in the mouth for the mounting of a healing connection. During the process, the position of the implant may be captured by physical molding or directly to the computer by means of a scanning process. For example, as described in U.S. Pat. No. 5,829,981 to Ziegler, entitled "One-Piece Impression Coping for Customized Implant Restorative Systems", the physical molding process, a printing workpiece capable of connecting the anti-rotation element of the implant, is stuck to it and the printing of the whole mandibular arch is made by capturing the workpiece. Afterwards, the printing is removed from mouth and a component similar to the implant is fixed to the same workpiece and the set gets a coat of plaster or a similar molding material so as to get a model of the patient's mandibular arch after the healing of the implant.

Typically, this step was followed by manual molding of the desired prosthetic component, generally in wax, for further casting in biocompatible metal (such as gold) and aligning problems were solve by adding intermediary components as those described in U.S. Pat. No. 4,988,297 to Lazzara et al, entitled "Alignment Corrector for Dental Implants". However, computer-aided design/computer-aided manufacturing (CAD/CAM) technologies for prosthetic components, for example as described in U.S. Pat. No. 4,742,464 to Duret et al., entitled "Method of Making a Prosthesis, Especially a Dental Prosthesis", and, particularly, from blocks that include the prefabricated anti-rotation element, as discussed in U.S. Pat. No. 6,991,853 to Branco de Luca, entitled "Blank From Which a Customized Prosthetic Part Can Be Machined", have paved the way for the manufacturing of connections through the computer without the need for manual molding or wax works.

For this purpose, generally, data about the position and orientation of the implant needs to be informed to the computer, which is done by means of intra-oral scanning, for example using laser infrared cameras or scanners, as described in U.S. Pat. No. 4,575,805 to Moermann et al., entitled "Method and Apparatus for the Fabrication of Custom-Shaped Implants", and in U.S. Pat. No. 4,837,732 to Brandestini et al., entitled "Method and Apparatus for the Three-Dimensional Registration and Di splay of Prepared Teeth".

However, it is difficult to work with scanning media directly inside the mouth, especially due to access difficulties, limited space, poor lighting, and the presence of fluids (such as saliva), which cause undesired reflexes that may affect the quality of the scanning and compromise the accuracy of the measurement. Capturing the anti-rotation element at the top of the implant when it might be hidden, in fluids or covered by close elements is particularly challenging, which frequently leads to errors that need to be later balanced.

In order to prevent errors, CAD/CAM system manufacturers started to employ measurement devices or scanning transfers, as indicated by reference number 35 in U.S. Pat. No. 8,480,396 to Saliger et al., entitled "Method for Automatically Fabricating a Dental Superstructure for Attachment to an Implant", which is intended to highlight the position and orientation of the implant for the scanning device. Such transfers, typically, may be placed in the mouth or over the plaster mold produced with the help of a printing piece, as previously performed. Generally, the advantage of the mold is the possibility of sending it to a laboratory when the dentist does not have the equipment for intra-oral scanning. The use of the mold as a basis for the scanning of the implant's position and orientation allows the use of scanning methods that are cheaper and larger, which cannot be used intra-orally.

Scanbodies used to determine the position and orientation of components as implants are endowed with a specific technique. For example, U.S. Pat. No. 8,747,112 to Brun, entitled "Abutment Position Locator", describes a workpiece to be fitted in a dental implant in an orientation that defines an 'X' insertion central axis and a 'D' insertion direction of the workpiece. According to Brun, the workpiece includes a flat bevel angle in its upper portion and a fit connection, and the implant has a resilient spring member in its lower portion for preventing its displacement relative to the implant when inserted into the dental implant.

For example, European Patent 2130514 to Scherberger, entitled "Abutment With Optically Detectable Elements Defining its Position and Orientation", describes a scanning item endowed with a beveled surface to enable optical scanning. According to Scherberger, the flat bevel angle extends itself over the length of the workpiece and its larger part is next to the base and its smaller part is closer to the top, and the width between the two edges decreases steadily. As discussed in Scherberger, the member is used solely for detection, and the same may be done in low-reflection material, reducing the need for adding non-reflective material.

As per the aforementioned documents, as well as according to components available in the market, state-of-the-art scanbodies use flat surfaces over a generally cylindrical body to determine the orientation of the implant and, specifically, the orientation of the anti-rotation element of the implant. This flat surface is generally in the form of a laminate or key way or, as a prismatic element comprised of multiple flat surfaces as discussed in European Patent 2218423 to Lawitschka et al., entitled "Determining Position and Orientation of a Dental Implant".

The problem with typical scanners is that its geometry generates artifacts, also referred to as errors, during scanning. Such artifacts occur due to the way the light emitted by scanners interacts with flat surfaces of the pieces. Such errors are compensated in a post-processing step, which prolongs the scanning process. Sometimes, when the measuring error is significant even after further processing, it is necessary to cover the piece with opaque sprays or non-reflective powder before a new measurement is performed.

Furthermore, when the piece does not present flat surfaces, as discussed in European Patent 2400917 to Eriksson et al., entitled "Device for Indicating the Position and Orientation of a Dental Implant", it is not possible to locate the orientation of the anti-rotation element on the abutment head. For example, the scanbody as presented in Eriksson et al., is also subject to problems in the identification of implant position and direction when it is set between remaining dental elements and only functions efficiently in the case of tooth loss.

Also, the material currently used in the making of scanners presents problems. Metal used in several aforementioned manners is expensive and presents shiny surfaces after machining. The plastic materials, on the other hand, are typically manufactured by an injection process to minimize costs. However, the injection process results in a nearly polished finishing, which highlights the shine problems, demanding the use of opaque sprays. Among the plastic materials used in the injection process, typically, natural Polyether Ether Ketone (PEEK) is one of the most widely used. However, generally, PEEK does not present good performance during the scanning process due to reflection. As such in view of the above, there is a need for a more efficient product, which may be totally and flawlessly scanned and which guarantees quality and accuracy to the scanning process in any type of scanner.

BRIEF SUMMARY OF THE INVENTION

One or more embodiments of the invention include a scanbody that provides improvements in scanbody performance based on raw material and external geometry. Regarding raw material, at least one embodiment of the invention includes an effect on opaque material that may be used in CAD/CAM scanners, which is used to dispense powder or spray application during a scanning process. Regarding geometry, one or more embodiments provide a geometry that favors the scanning in all regions of the mouth with the correct identification of a position, direction and rotation of the implant or implant analogs. In at least one embodiment, the scanbody may be asymmetrical to ensure the correct identification of the position, direction and rotation of the analogs, without generating any asymmetry measurement errors.

One or more embodiments of the invention include a scanbody geometry used during a scanning procedure that minimizes, or eliminates, the formation of artifacts, such as errors, during the scan. As such, in at least one embodiment, the accuracy and reliability of the scanning of models with analogs is increased, thus facilitating the manufacture of prosthetic structures. At least one embodiment of the invention may eliminate the use of non-reflective powders or opacificator sprays during the scanning process.

One or more embodiments of the invention may include assembling a scanbody that only includes rounded surfaces on the face of the scanbody to determine the rotational orientation of the workpiece and applying a dual-taper geometry design to the scanbody. At least one embodiment may include rounded surfaces instead of flat surfaces, such that the quality of data collection is improved, since such surfaces decrease the incidence of reflections on the scanner's capture element. One or more embodiments of the invention may include dual-taper geometry that forms the scan body, to enlarge the reading area without generating unwanted reflections, and to determine workpiece height more precisely. In at least one embodiment, the ability to recognize geometry may conveniently affect software needed for the scanning process, wherein less error correction routines are required during the scanning procedure.

One or more embodiments of the invention may include machining the part instead of manufacturing it by injection molding, wherein micro grooves resulting from the machining process helps increase scanbody surface opacity.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1A:
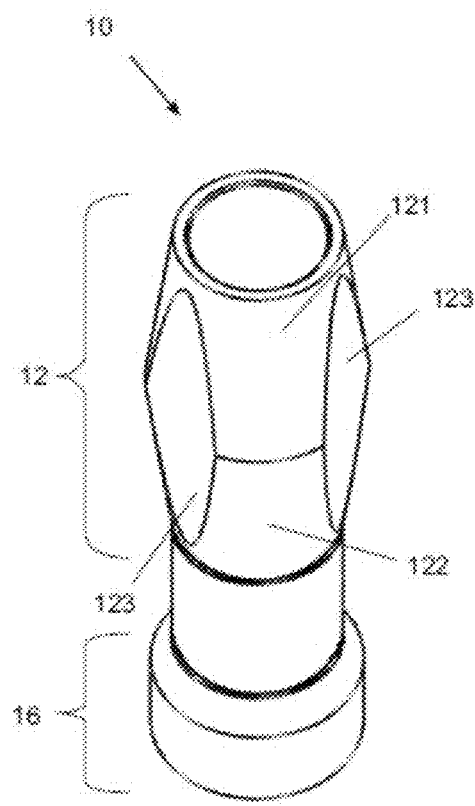
FIGS. 1A and 1B illustrate main features of a scanbody and a cross-sectional view of the scanbody.
Figure 1B:
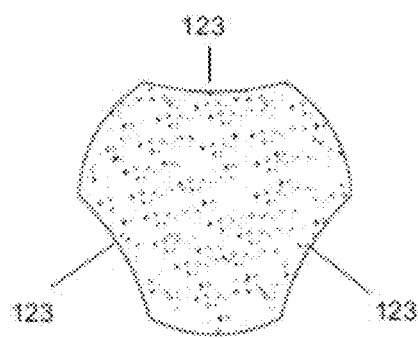

FIGS. 1A and 1B illustrate the main features of the scanbody device and a cross-section view of the scanbody device, according to one or more embodiments of the invention. At least one embodiment includes a scanning device (10) that includes a body (12) and a base (16) interconnected by a middle part to maintain a body and base set height constant when different types of anti-rotation elements are used.

In one or more embodiments, the base (16), as a lower part of the scanning device (10), may fit on a dental implant anti-rotation geometry, whether located in a fixing installed in a mouth of a user or analog attached to a plaster model. It is noted wherein FIGS. 2A, 3, 4, 5, and 6 illustrate the related elements as shown in FIGS. 1A and 1B, as different base geometries (16, 26, 36, 46, 56, 66) that may be used, relating to a type of abutment coupling geometry used in one or more embodiments of the invention.

In at least one embodiment, the body (12) may include, or may be formed by, a dual-taper geometry, specifically may include or may be formed by two truncated cones joined or coupled base-to-base, referred to herein as primary and secondary trunconical elements. In one or more embodiments, the main feature of the body (12) may include a dual-trunconical assembly without any flat surface.

Figure 7B:
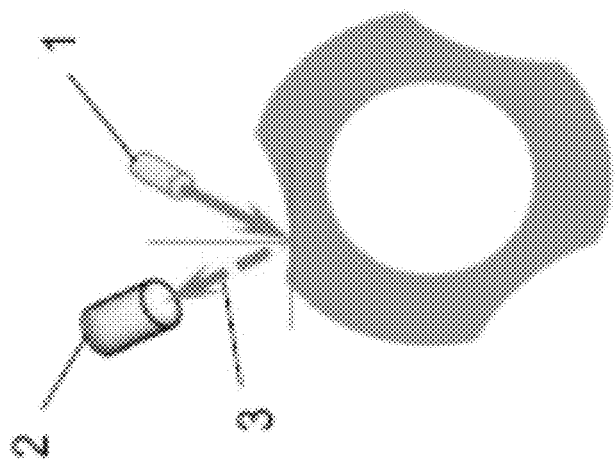
FIGS. 7A and 7B illustrate the effect achieved by the surfaces of the scanbody during a scanning procedure.
Figure 7A:
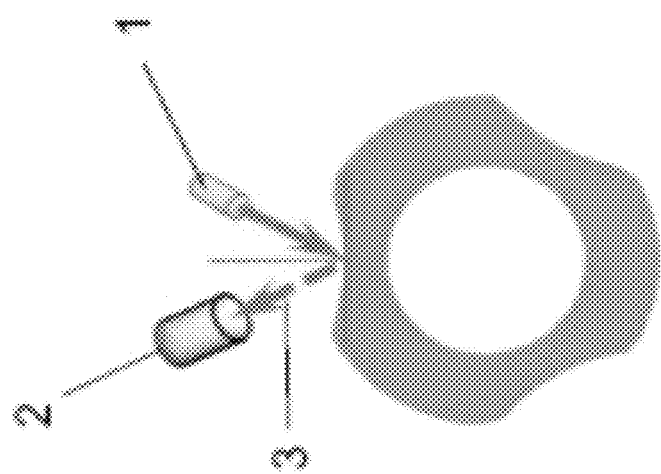

At least one embodiment may include rounded surfaces, as shown in FIGS. 7A and 7B, that may be irradiated by a source of light (1) and may include at least one light reflection point that carries part of the light waves reflected (3) towards a receiver (2). In one or more embodiments, the time range between light wave emission and detection may be used to measure the distance traveled and, consequently, the geometry of the workpiece being scanned.

Figure 8B:
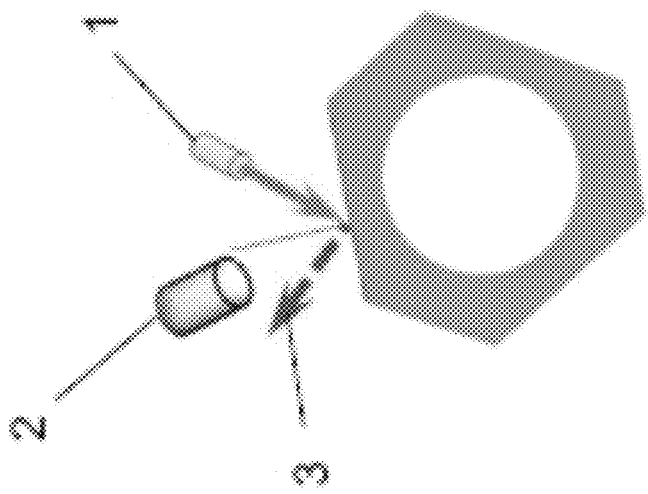
FIGS. 8A and 8B illustrate a typical prior art technique issue during a scanning procedure.
Figure 8A:
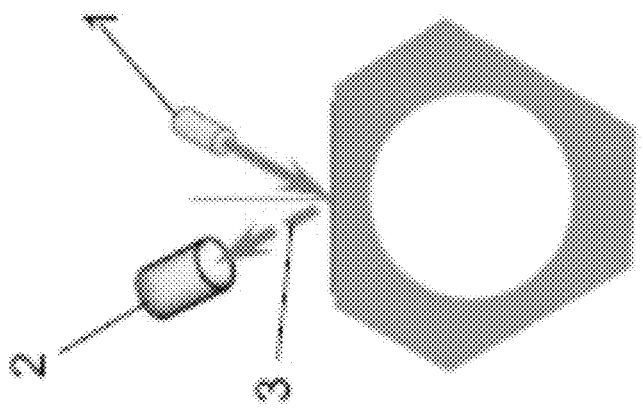

Typically, when a workpiece includes flat surfaces, as shown in prior art FIGS. 8A and 8B, at some points no wave (3) irradiated by a source of light (1) reaches the receiver (2), resulting in a measurement fault. Generally, the measurement fault results in geometry estimation errors when seen as irregular spots on the surface of the scanned part when displayed on a computer. In extreme cases, typically, such reading errors are enough to mask the exact geometry leading to a manufacturing failed prosthetic element that needs to be corrected after manufacture.

Generally, a prior art technique corrects such errors with post processing steps using the computer, which requires more sophisticated computer programs and longer processing time. One or more embodiments of the invention resolve such a measurement fault and errors by changing the geometry of the scanbody.

By way of at least one embodiment, the body (12, 22, 32, 42, 52, 62) of the scanbody may be arranged such that the scanner reading always display an opposing primary trunconical element (121, 221, 321, 421, 521, 621) coupled base-to-base to a secondary trunconical element (122, 222, 322, 422, 522, 622).

In one or more embodiments, the dual-trunconical geometry may increase the reading area, such that the implant position may be determined, particularly when installing the implant in the mouth of the user. In at least one embodiment, the greater reading area may increase implant position transfer during scanning to minimize settlement failure problems of the final prosthesis.

Figure 6:
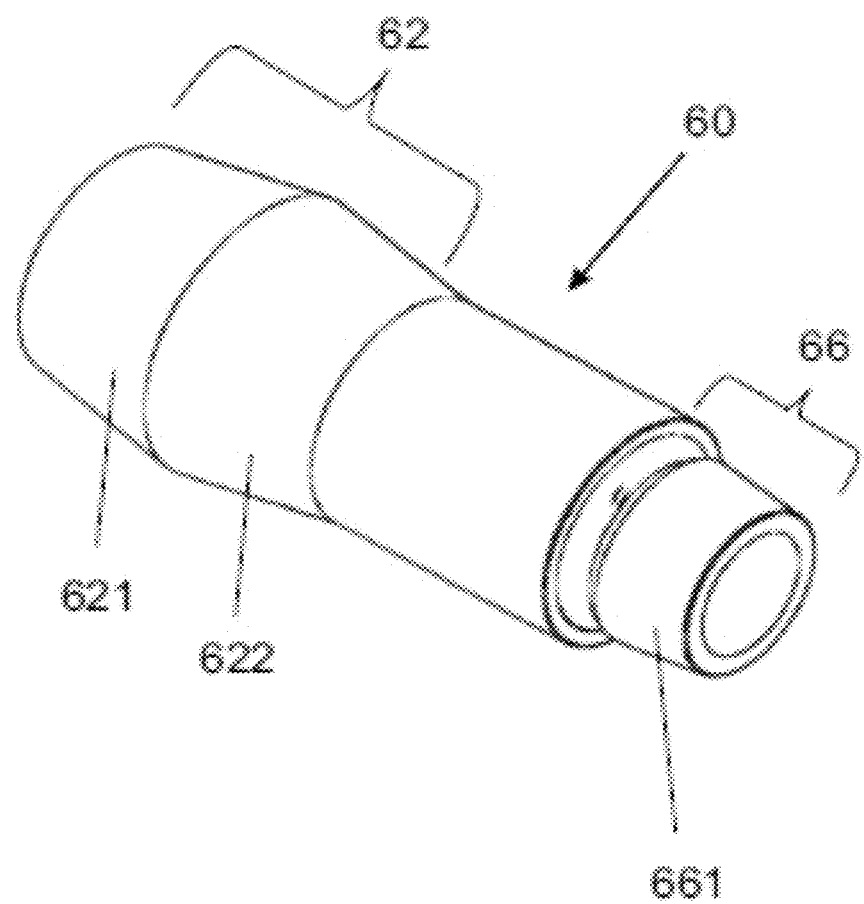

One or more embodiments of the invention, for example, may include bridges, which are prostheses supported on multiple implants in which the body, with two trunconical elements, may be enough to detect implant position and direction information. In at least one embodiment, the scanbody may include multiple supporting points, such that the prosthetic element does not depend on the anti-rotation geometry found in the head of the implant to ensure its alignment within the mouth in order to detect the implant position and the direction information. FIG. 6 illustrates the scan component that may be used, according to one or more embodiments of the invention.

In at least one embodiment, for example used during a single tooth replacement, the rotating location of the anti-rotation element may be determined, in addition to the position and direction, such that the prosthetic component is placed in the same position to be aligned with the rest of the dental arch. One or more embodiments, such as the lateral surface of the body, may include concave surfaces (123, 223, 323, 423, 523) arranged in the side of the body (12, 22, 32, 42, 52), such that the rotational information may be measured without the use of flat surfaces.

Figure 2A:
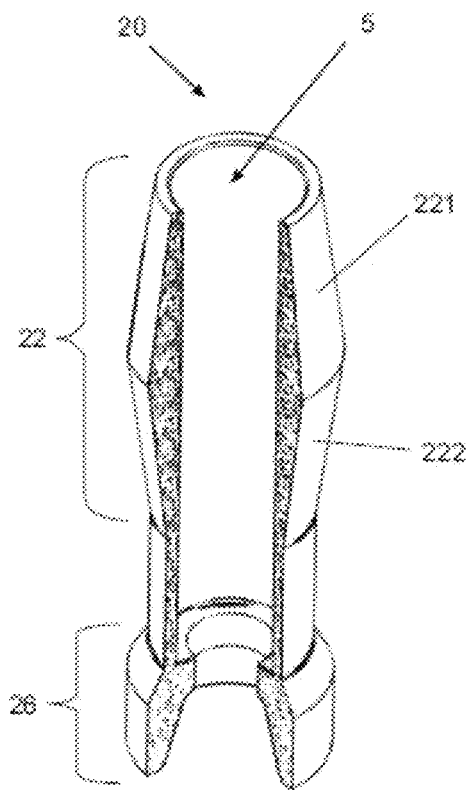
FIGS. 2A and 2B illustrate the scanbody with a hole access to fix a screw.
Figure 2B:
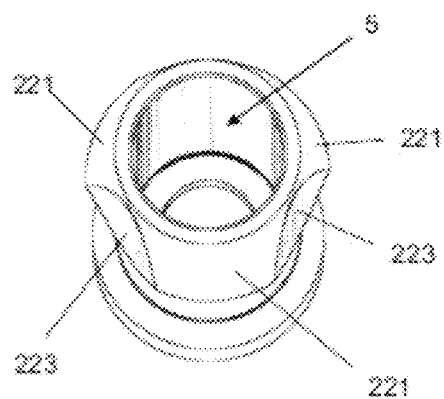

FIGS. 2A and 2B illustrate a scanbody according to one or more embodiments of the invention. As shown in FIGS. 2A and 2B, at least one embodiment of the invention may include a hole (5) and a channel that fits a fixing screw. By way of one or more embodiments, the fixing screws may ease the scanbody attachment to the implant, either in the user's mouth or in the model, and thus displacements during scanning are avoided.

Figure 3:
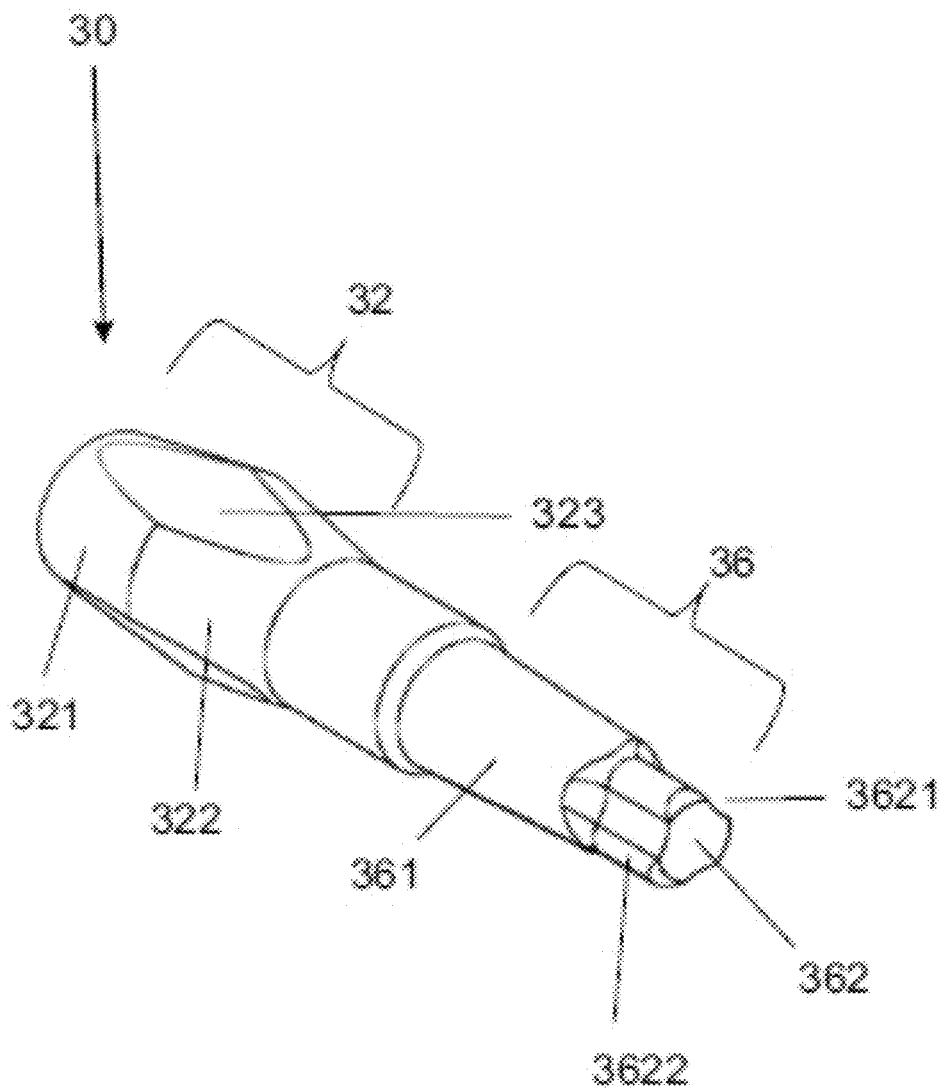
FIGS. 3, 4, 5 and 6 illustrate the scanbody provided with different coupling elements.
Figure 4:
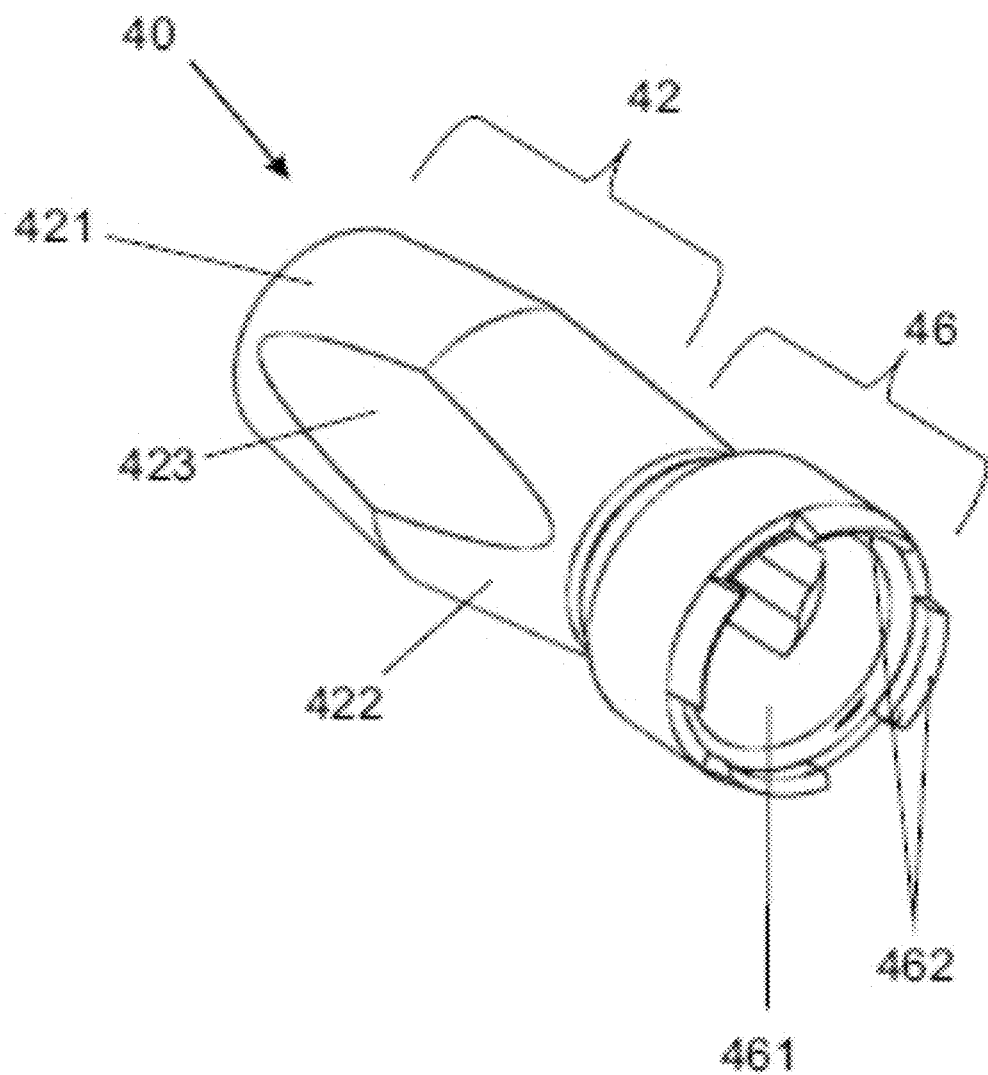
Figure 5:
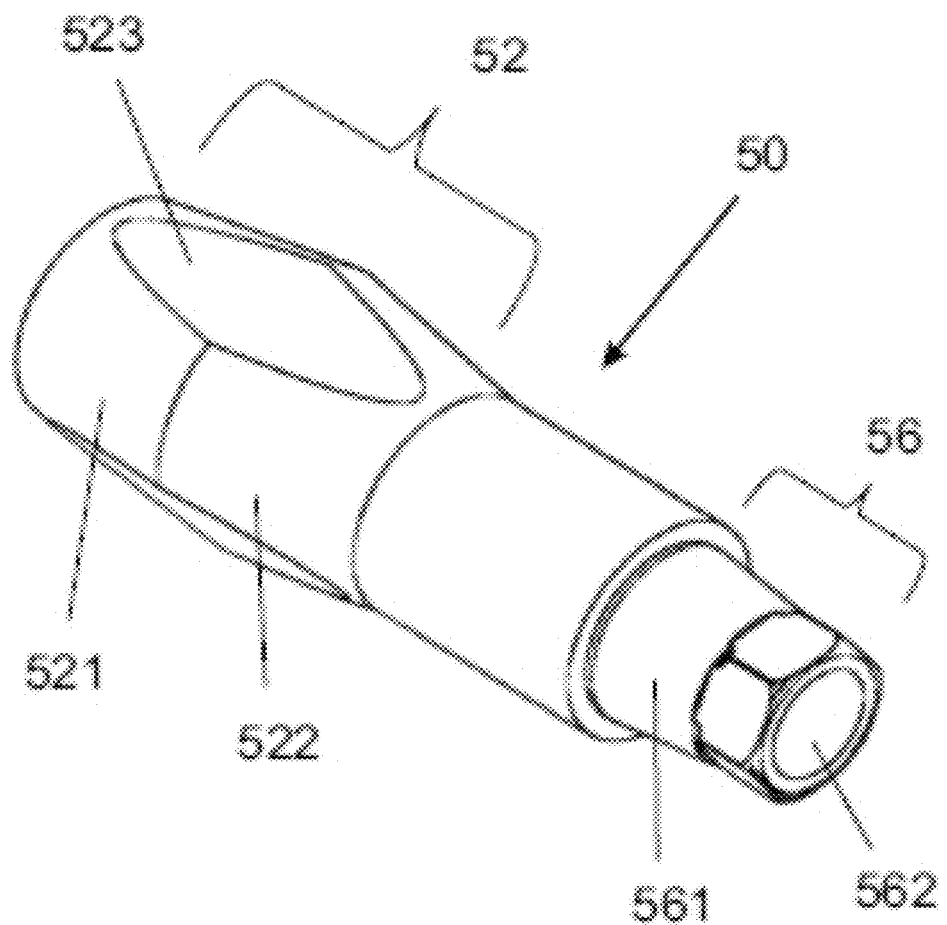

FIGS. 3, 4, 5 and 6 illustrate the scanbody with different coupling elements in its base, according to one or more embodiments of the invention. As shown in FIGS. 3, 4 and 5, at least one embodiment of the invention may include anti-rotation coupling geometries. As shown in FIG. 6, one or more embodiments of the invention may include rotating coupling geometry. In at least one embodiment, the anti-rotation coupling geometries may be used with the prosthesis supported on multiple implants when the position of the anti-rotation implant element is not relevant.

FIG. 3 illustrates the scanbody (30) with Morse taper (361) anti-rotation geometry on its base (36), according to one or more embodiments of the invention. As shown in FIG. 3, in at least one embodiment, the Morse taper (361) anti-rotation geometry may include or may be coupled to a prism (362) with three concave sides (3621) lodged within three convex sides (3622).

FIG. 4 illustrates the scanbody (40) with Universal type (461) anti-rotation geometry at the base (46), according to one or more embodiments of the invention. In at least one embodiment, the scanbody may be coupled to different types of anti-rotation geometries that include scanbody fastening clamps (462) used during the scanning procedure.

FIG. 5 illustrates a scanbody (50) with Morse taper (561) type anti-rotation geometry on the base (56), according to one or more embodiments of the invention. As shown in FIG. 5, in at least one embodiment, the Morse taper (561) type anti-rotation geometry may include or may be coupled with a hexagonal prism (562). FIG. 6 illustrates the scanbody (60) with straight trunconical (661) rotation coupling geometry at the base (66), according to one or more embodiments of the invention. As shown in FIG. 6, in at least one embodiment, the straight trunconical (661) rotation coupling geometry may be used when multiple implants are used to support, for example, a prosthetic bridge, as previously mentioned, wherein rotating orientation information may not be relevant.

According to one or more embodiments, the scanbodies may be or may include different opaque materials, or the different opaque materials may be used to produce the scanbodies, using the geometry as discussed herein. In at least one embodiment, the opaque materials may be biocompatible and may be autoclaved to disinfect and to minimize the occurrence of problems when the scanbodies are used in an intraoral environment.

One or more embodiments of the invention may be applied to PEEK-Classix™ white resin, developed by Invibio®, and life science grade by-products such as Ketron® PEEK LSG plastic, whose opacity characteristics are higher than those of natural PEEK. By way of at least one embodiment, to improve the scanbody opacity characteristics for the present invention, the scanbody may be machined instead of injection molded. According to one or more embodiments, the micro surface resulting from the machining process may lower reflectivity (greater opacity) of the work piece.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A scanbody consisting of:
a base with a coupling geometry configured to fit a geometry of a dental implant coupling, and
a body configured to be scanned, wherein the body consists of a height and a lateral surface consisting of two geometrical elements that allow identification of information of a position, a direction and a rotation of the scanbody,
wherein
the lateral surface of said body does not comprise any flat areas,
said two geometrical elements of said lateral surface form the height of said body,
said two geometrical elements consist of a dual-trunconical assembly formed by two opposing truncated cones coupled base-to-base,
said two opposing truncated cones consist of
a primary trunconic element, and
a secondary trunconic element coupled to the primary trunconic element, such that the primary trunconic element is aligned with a longitudinal axis of the secondary trunconic element, and
the lateral surface of the body further consists of at least one concave surface that overlaps both said primary trunconic element and said secondary trunconic element.

2. The scanbody according to claim 1, further consisting of a hole configured to receive a fixing screw inserted therein.

3. The scanbody according to claim 1, wherein the coupling geometry of the base consists of a Morse taper geometry that includes a surface with three concave sides lodged by three convex sides.

4. The scanbody according to claim 1, wherein the coupling geometry of the base consists of a universal geometry that includes fastening clamps to secure the scanbody.

5. The scanbody according to claim 1, wherein the coupling geometry of the base consists of a Morse taper geometry that includes a hexagonal prism.

6. The scanbody according to claim 1, wherein the coupling geometry of the base consists of a straight trunconic geometry.

7. The scanbody according to claim 1, wherein the scanbody is a biocompatible material.

8. The scanbody according to claim 1, wherein the scanbody is a polyether ether keton material configured for applications in medical, pharmaceutical and biotechnology markets.

9. The scanbody according to claim 1, wherein said base and said body consist of a predefined height.

* * * * *